United States Patent [19]

Nauroth et al.

[11] Patent Number: 4,857,289

[45] Date of Patent: Aug. 15, 1989

[54] PROCESS FOR PREPARING PRECIPITATED SILICA

[75] Inventors: Peter Nauroth, Wesseling; Robert Kuhlmann, Erftstadt; Gunter Turk, Hanau; Adam Becker, Bornheim-Hersel, all of Fed. Rep. of Germany

[73] Assignee: Degussa Aktiengesellschaft, Frankfurt, Fed. Rep. of Germany

[21] Appl. No.: 191,751

[22] Filed: May 5, 1988

Related U.S. Application Data

[63] Continuation of Ser. No. 852,595, Apr. 16, 1986, abandoned, which is a continuation of Ser. No. 674,883, Nov. 26, 1984, abandoned.

[30] Foreign Application Priority Data

Apr. 10, 1981 [DE] Fed. Rep. of Germany ....... 3114493

[51] Int. Cl.$^4$ .............................................. C01B 33/93
[52] U.S. Cl. ..................................... 423/339; 423/335
[58] Field of Search ................................. 423/335, 339

[56] References Cited

U.S. PATENT DOCUMENTS

| | | | |
|---|---|---|---|
| 4,040,858 | 8/1977 | Wason | 423/339 |
| 4,076,549 | 2/1978 | Wason | 423/339 |
| 4,144,321 | 3/1979 | Wason | 423/339 |
| 4,312,845 | 1/1982 | Wason | 423/339 |

*Primary Examiner*—Jack Cooper
*Attorney, Agent, or Firm*—Beveridge, DeGrandi & Weilacher

[57] ABSTRACT

Precipitated silicas which have the following physico-chemical characteristics, depending on the manner in which they are milled:

| | | Pendulum roller mill | Jet mill |
|---|---|---|---|
| BET surface area | m$^2$/g | 15–110 | 15–110 |
| Tamped density | g/l | 150–750 | 90–650 |
| Cu abrasion in 10% strength glycerol dispersion | mg | 5–30 | 5–30 |
| Lightness value A | % | 86–96 | 90–96 |
| Particle size distribution curve determined by a Coulter Counter | | as in FIG. 1 | as in FIG. 2 |
| "ALPINE screen retainings" >63 μm | % by weight | <1.5 | <0.1 |
| Viscosity of a 30% strength dispersion in a 1:1 glycerol/water mixture (Brookfield RTV, Sp5) | mPa.s | 30,000 | to 60,000 | are prepared by diluting a precipitated silica original suspension obtained according to German Published Application DAS 1,467,019 and simultaneously adding alkali metal silicate solution, sulfuric acid and water while keeping the pH constant between 7 and 9. The precipitated silica is then filtered off, washed, dried and milled using a pendulum roller mill or a jet mill.

Because of their abrasiveness, the precipitated silicas can be employed as cleansing and abrasive agents and, in the case of the jet-milled product, also as a polishing agent, abrasive and thickener in toothpastes.

8 Claims, 3 Drawing Sheets

PROCESS FOR PREPARING PRECIPITATED SILICA

This application is a continuation of application Ser. No. 852,595, filed Apr. 16, 1986, which is a continuation of application Ser. No. 674,883, filed Nov. 26, 1984, which is a continuation of application Ser. No. 364,096, filed Mar. 31, 1982, all now abandoned.

A number of processes for the preparation of low-structure precipitated silicas have been disclosed:

According to German Laid-Open application DOS 2,344,316, a prepolymerized sodium silicate solution is first prepared by adding 5–10% by weight of sodium sulfate to the sodium silicate solution and then precipitating the silica by adding acid, or by taking a portion of the prepolymerized sodium silicate solution, adjusting its pH with acid to a value between 6.5 and 11, and then precipitating the silica by simultaneous addition of sodium silicate solution and acid at a constant pH.

German Laid-Open application DOS 2,344,805 describes a process wherein an alkali metal silicate solution is acidified until silica begins to precipitate, the addition of acid is then stopped, the reaction solution is aged for up to four hour and thereafter simultaneous addition of acid and of alkali metal silicate is continued until the desired product is obtained.

German Laid-Open application DOS 2,446,038 describes a method of preparation wherein a prepolymerized sodium silicate solution containing 7% by weight of added electrolyte, and dilute (10–25% strength by weight) acid are added simultaneously, at pH 9 and at 65° C., to an electrolyte-containing initial charge of 3–15% by weight sodium sulfate solution. After the addition, the pH is brought to below 5 and the mixture is aged for twenty minutes at 77° C.

German Laid-Open application DOS 2,522,486 describes the preparation of a precipitated silica by employing a portion (8–50%) of the total alkali metal silicate solution employed as an initial charge into which alkali metal silicate solution and acid are run simultaneously until, on termination of the addition of alkali metal silicate and of acid, 20–500% of the amount of the original charge of alkali metal silicate solution have been converted. Thereafter, the pH is reduced to below 6. Dilute sulfuric acid (8–22% by weight) must be used.

According to the process disclosed in German patent application S 35,743 IVa/12i of 3.10.1953, precipitation is effected onto a 2% strength by weight dispersion prepared from a "light silica" (preparation not disclosed) and water, at 80° C. and in the pH range of from 7 to 7.5, by means of dilute sodium silicate solution (density=1.152) and dilute hydrochloric acid (2N), over a period of 2 hours. Thereafter, the mixture is diluted with water. The silica obtained is distinguished by a very low bulk density.

Although the processes of preparation referred to above give low-structure silicas, these methods have certain disadvantages which make their industrial implementation relatively involved and uneconomical compared to the conventional methods for obtaining reinforcing silicas for rubber. The disadvantages are:

the introduction of an additional component step for the preparation of silica-containing or electrolyte-containing initial precipitation charges from electrolyte-containing precipitation reactants and the marked reduction in space-time yield in the precipitation of such silicas, as a result of the need to introduce an interruption interval (ie. an aging step), and also as a result of the use of dilute reactants and of the need for long precipitation times.

Accordingly, there exists an industrial requirement for a method of preparing low-structure precipitated silicas by a simple, economical, optimized method which fits in with the sequence of the reinforcing filler production methods.

It is known from German published application DAS 1,467,019 that amorphous precipitated silicas may be obtained by simultaneously adding acid and alkali metal silicate solutions to an alkaline initial charge, provided certain process conditions are observed. Precipitated silicas obtained by this process may be classified as materials having a relatively high structure (relatively high oil absorption), relatively high specific surface area, low bulk density and low solids content in the filter cake. Because of their excellent dispersibility in rubber mixtures, they are preferred reinforcing fillers in the rubber industry, in which they are used extensively for the production of rubber soles, tire treads and industrial articles, with or without the use of a silane. As reinforcing standard fillers, and as the main products of any filler factory, this type of precipitated silica is continuously available, day in and day out. This availability also applies to the original precipitation suspension, which is stored as an intermediate in large suspension storage tanks before being fed to the filter presses in order to have the electrolyte removed.

We have found, surprisingly, that an original precipitated silica suspension obtained by the method of German published application DAS 1,467,019 can be used as a cheap starting product for obtaining precipitated silicas having a low structure and high hardness, even coupled with great fineness, if certain measures are followed during subsequent modification and further processing. In this way it proves possible to avoid entirely the technically involved, additional and frequently uneconomical preparation of salt solutions which serve as the initial charge for the precipitation, as well as the economically entirely unacceptable redispersion of already dried precipitated silica powders to form silica dispersions for use as the initial precipitation charge, and also the preparation of electrolyte-containing alkali metal silicate solutions or acid solutions; accordingly, the existing processes of the prior art can be substantially simplified and cheapened. Similar remarks apply as regards the other disadvantage, namely the low space-time yield, since, in the process according to the invention, it is possible to work without interruption intervals, with relatively short precipitation times and with concentrated reactants.

The present invention provides precipitated silicas which are characterized by the following data, depending on their degree of milling:

|  |  | Pendulum roller mill | Jet mill |
|---|---|---|---|
| BET surface area determined according to DIN 66,131 | m²/g | 15–110 | 15–110 |
| Tamped density determined according to DIN 53,914 | g/l | 150–750 | 90–650 |
| Cu abrasion in 10% strength glycerol dispersion | mg | 5–30 | 5–30 |
| Lightness value A according to DIN 55,921 | % | 86–96 | 90–96 |
| Particle size distribution curve according to FIG. 1 |  |  |  |

| | Pendulum roller mill | Jet mill |
|---|---|---|
| or FIG. 2, using the Coulter Counter | | |
| "ALPINE screen retainings" >63 μm % by weight | <1.5 | <0.1 |
| Viscosity of a 30% strength dispersion in a 1:1 glycerol/water mixture (Brookfield RTV, Sp5) mPa.s | 30,000 | to 60,000 |

The invention is further illustrated by the drawings wherein.

The precipitated silicas according to the invention exhibit the following advantageous properties:

The high tamped densities, which are three times as high as those of the conventional precipitated silicas for rubber reinforcement, substantially reduce the expenditure on packaging material, packaging operations, transportation and storage. During processing, the user benefits from the relatively low volumes involved.

The high and precisely selectable Cu abrasion value allows the product to be used as an abrasive and cleansing agent. We have found, surprisingly, that the abrasiveness does not, as is usual, diminish progressively with increasing fineness of a given silica base material, so that the combined properties of abrasiveness and great fineness make this silica a valuable filler for toothpastes. The fact that the abrasiveness is maintained when the material is very fine accordingly permits the use of jet mills (air jet mills or steam jet mills) which, as a result of the principle of predominantly mutual particle size reduction, avoids abrasion of the walls of the milling equipment and therefore yields lighter colored, purer end products than those obtained from mills equipped with mechanical impact tools.

A particularly interesting feature for use of the precipitated silica according to the invention as a polishing agent in toothpastes is the unique combination of abrasiveness and thickening action. This combined property, which is only observed in the case of the jet-milled finely divided form of the product, makes it possible for the cosmetics industry to manage with only a single silica component, and in most cases also with smaller amounts than hitherto.

Figure 1:
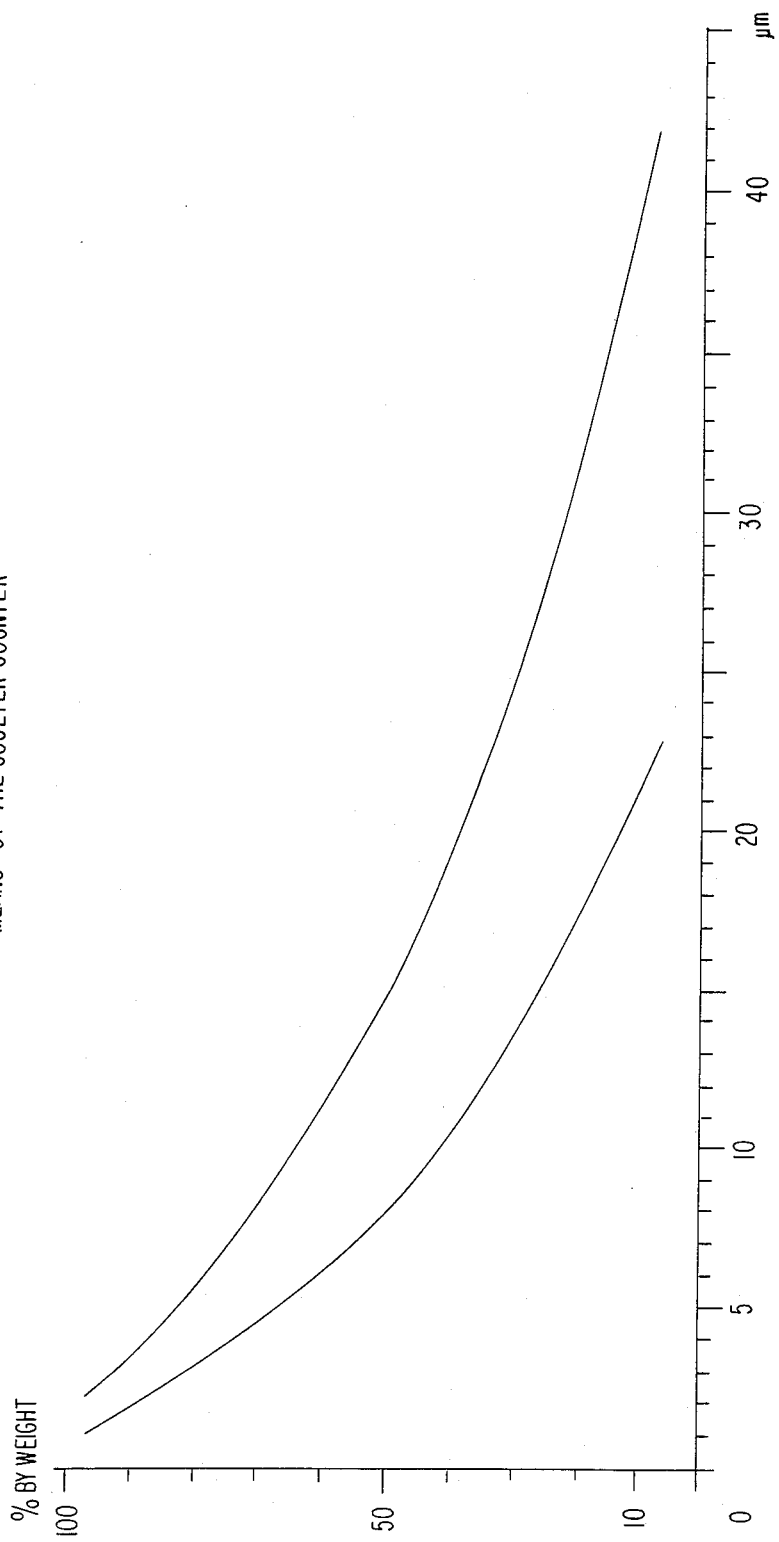
FIG. 1 is a particle size distribution curve.
Figure 2:
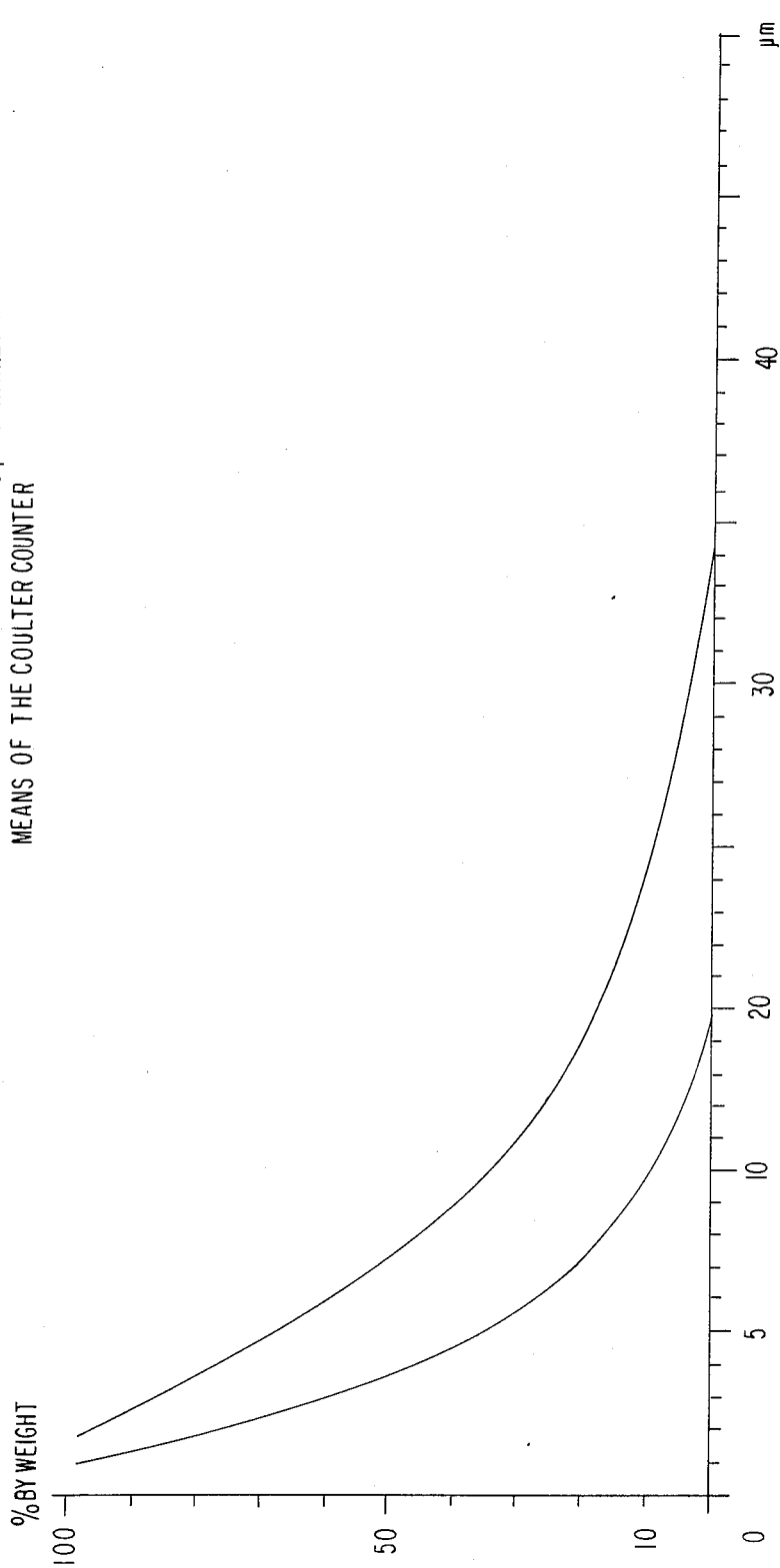
FIG. 2 is a particle size distribution curve.
Figure 3:
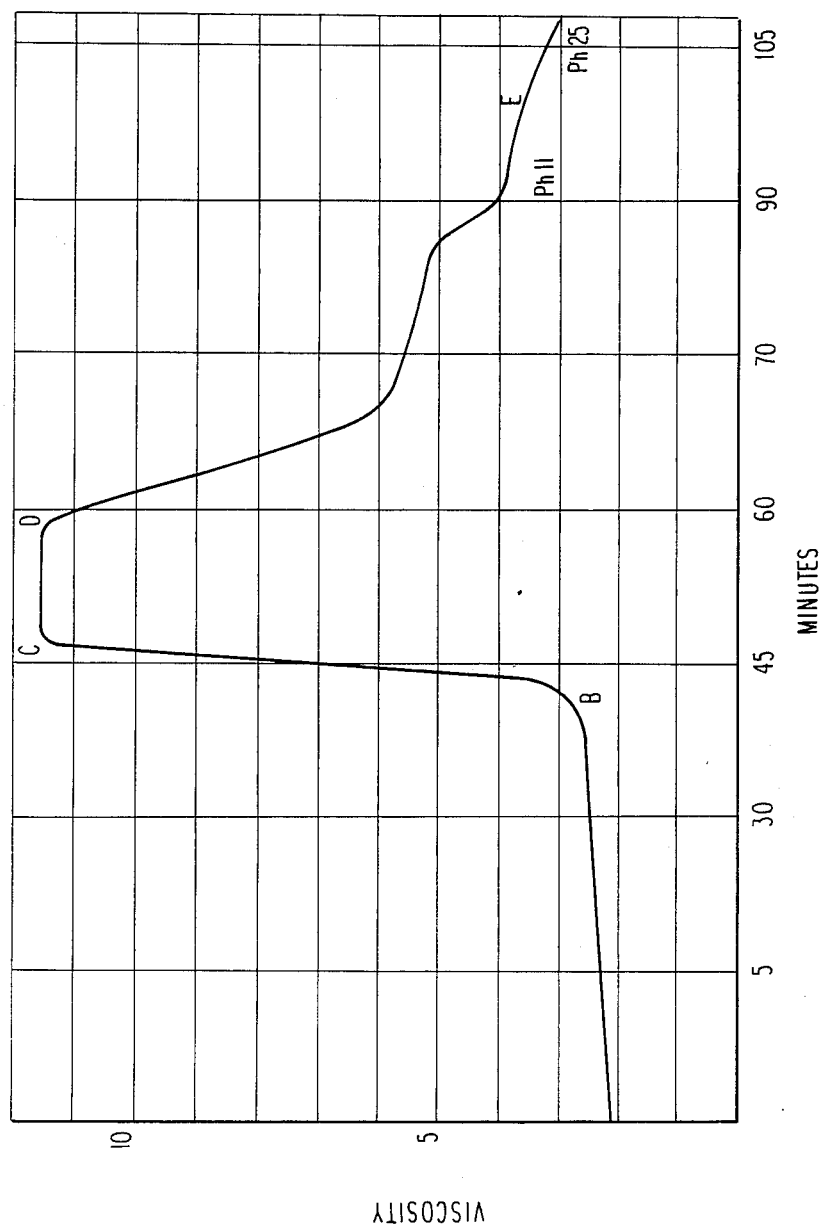
FIG. 3 is a plot showing the change in viscosity with time at constant pH.

The invention further relates to a process for the preparation of the precipitated silicas according to the invention, having the following physicochemical characteristics, depending on the degree of milling:

| | | Pendulum roller mill | Jet mill |
|---|---|---|---|
| BET surface area determined according to DIN 66,131 | m²/g | 15–110 | 15–110 |
| Tamped density determined according to DIN 53,194 | g/l | 150–750 | 90–650 |
| Cu abrasion in 10% strength glycerol dispersion | mg | 5–30 | 5–30 |
| Lightness value A according to DIN 55,921 | % | 86–96 | 90–96 |
| Particle size distribution curve according to FIG. 1 or FIG. 2, using the Coulter Counter | | | |
| "ALPINE screen retainings" >63 μm | % by weight | <1.5 | <0.1 |
| Viscosity of a 30% strength dispersion in a 1:1 glycerol/water mixture (Brookfield RTV, Sp5) | mPa.s | 30,000 | to 60,000 | wherein an original precipitated silica suspension which is prepared by precipitating the silica in an initial charge of alkali metal silicate solution, having a concentration of about 5–25 g of $SiO_2$ per liter of solution, by means of an acid and alkali metal silicate solution of particular concentrations, at particular feed rates, while maintaining a precipitation temperature in the reaction medium between 80° and 90° C., the precipitation being carried out under such conditions that the viscosity of the reaction medium is kept, for at least 30% of the total precipitation time, at a uniform low value while the pH is kept between 10 and 12, and the addition of the reactants only being terminated when the viscosity, after passing through a maximum, has dropped to a value which is less than 100% above the initial value, is diluted with hot water to a precipitated silica content of 10–30 g/l and a sodium sulfate content of 6–20 g of $Na_2SO_4$/l, and heated to 85°–95° C., the pH is brought to 7–9 with sulfuric acid and, while keeping this pH value constant, alkali metal silicate solution, sulfuric acid and, if necessary, hot water are added simultaneously over a precipitation period of 15 to 180 minutes so as to give a final concentration of precipitated silica of 40 to 80 g/l, the suspension is acidified with concentrated sulfuric acid to a pH below 7, and the precipitated silica is separated from the suspension by means of a filter press, washed out, dried and milled by means of a pendulum roller mill or jet mill.

In a preferred embodiment, it is possible to use an original precipitated silica suspension which, during its preparation according to German published application DAS 1,467,019, is subjected to intensive shearing action. This is of advantage whenever particularly high bulk densities and high Cu abrasion values are to be obtained. In a particular embodiment of the invention, the shearing can be effected according to Germn Pat. No. 1,767,332.

In the alkali metal silicate solution employed, the weight ratio of $SiO_2:Na_2O$ can be from 2 to 4. In a preferred embodiment of the invention, the alkali metal silicate solution can have a concentration of 8.0% by weight of $Na_2O$ and 26.8% by weight of $SiO_2$. This corresponds to a weight ratio of $SiO_2:Na_2O$ of 3.46.

In the course of the simultaneous addition of alkali metal silicate solution, sulfuric acid and, if necessary, hot water, the amounts added per hour per 10 liters of precipitated silica suspension may be from 0.5 to 10 liters of alkali metal silicate solution of density 1.353 and having an $SiO_2:Na_2O$ ratio of 3.46, from 0.05 to 1 liter of 96% strength sulfuric acid and up to 10 liters of hot water.

The concentration of sulfuric acid employed can be up to 96% by weight; in a preferred embodiment, it is 50% by weight.

The process for the preparation of the precipitated silica according to the invention has the following advantages:

the high solids content in the filter cake, namely up to 50% by weight, reduces the energy required for the drying process and accordingly the drying costs to about 25% of the values which apply to the reinforcing silicas used in the rubber industry, the high solids content in the filter cake, namely up to 50% by weight, doubles the filter press capacity, the relatively low specific surface area of the low-structure precipitated silica results in markedly reduced washing times and hence in savings of wash water and in additional filter press capacity and it proves possible deliberately to select the principal material data of the silica according to the invention.

The examples which follow illustrate and describe the precipitated silica according to the invention, and the process for its preparation:

EXAMPLE 1

(Comparative Example)

This example describes the preparation of a precipitated silica according to German published application DAS 1,467,019.

73 liters of hot water and 5.25 liters of sodium silicate solution (density: 1.353 g/ml; $SiO_2:Na_2O$ ratio=3.46) are heated, with stirring, to 85° C. in a rubber-lined 120 liter precipitation vessel. During the next 90 minutes, sodium silicate solution (density=1.353 g/ml; $SiO_2$:$Na_2O$ ratio=3.46) at 11 liters/hour, and concentrated (96% strength) sulfuric acid, at 0.965 liter/hour, are metered simultaneously into the initial alkaline precipitation charge, with stirring and while maintaining the temperature at 85° C. The precipitated silica suspension is then brought to a pH of 8.5 by means of concentrated (96% strength) sulfuric acid, through introducing the acid at the rate of 1.25 liters/hour over a period of several minutes. The precipitated silica suspension thus obtained has a solids content of about 85 g/l. Its $Na_2SO_4$ content is about 55 g/l. It is employed as a so-called "original precipitated silica suspension" for the preparation of the precipitated silicas according to the invention, described in the examples which follow.

In the further course of the above process, the precipitated silica suspension is acidified to a pH of 3.5 with concentrated (96% strength) sulfuric acid and the precipitated silica is then isolated from the suspension by means of a laboratory filter press, and the filter cake is washed with water, dried at 110°–120° C. and milled using a laboratory pinned disk mill. The physicochemical data are shown in Table I.

EXAMPLE 2

The "original precipitated silica supension" of Example 1 is diluted with sufficient water to give a precipitated silica content of 20 g/l and an $Na_2SO_4$ content of 13 g/l.

10.5 liters of this suspension are heated to 85° C., with stirring, in a rubber-lined 30 liter precipitation vessel. While maintaining this temperature and a pH of 8.5, the following are added simultaneously to the precipitated silica suspension over a period of 30 minutes: waterglass solution (8.0% of $Na_2O$ and 26.8% of $SiO_2$; density: 1.353 g/ml; $SiO_2:Na_2O$ ratio=3.46), at a rate of 92.4 ml/min., sulfuric acid (50% strength) at a rate of 19.6 ml/min and water at a rate of 185.4 ml/min. The precipitated silica suspension is then brought to a pH of about 3.5 with sulfuric acid (50% strength). At the end of the precipitation time, the precipitated silica content of the suspension is 64 g/l. The silica obtained is isolated from the suspension by means of a laboratory filter press, the filter cake is washed salt-free with water and is dried at 110°–120° C., and the product is milled on a laboratory pinned disk mill. The characteristic data are shown in Table I.

EXAMPLE 3

The procedure described in Example 2 is followed, but the simultaneous dosage of the waterglass, sulfuric acid and water is halved. By adopting this measure, the tamped density can be virtually doubled compared to that of Example 2, while the abrasiveness is markedly reduced. The precipitated silica content of the suspension is 49 g/l. The characteristic data are shown in Table I.

EXAMPLE 4

The procedure followed is as in Example 3, except that the precipitation time is increased from 30 to 60 minutes. The precipitated silica content is found to be 64 g/l. The tamped density is markedly higher than that of the precipitated silicas obtained in Examples 2 and 3. This is also true of the Cu abrasion. The characteristic data are shown in Table I.

EXAMPLE 5

The procedure of Example 4 is followed, but the precipitation time is increased from 60 to 120 minutes. Parallel thereto, the simultaneous dosage of the waterglass, sulfuric acid and water components is halved. The dosage is: waterglass: 23.1 ml/min; sulfuric acid: 4.9 ml/min; water: 46.35 ml/min. The precipitated silica content assumes the value of 64 g/l. The tamped density and abrasiveness are once again higher. The characteristic data are shown in Table I.

EXAMPLE 6

The procedure of Example 4 is followed, except that the "original precipitated silica suspension" from Example 1 is only diluted to 30 g of precipitated silica/l and about 20 g of $Na_2SO_4$/l. 10.5 liters of this suspension are used for the subsequent precipitation. The resulting precipitated silica content is 71 g/l. The tamped density and abrasion decrease slightly compared to the data of the precipitated silica of Example 4. The characteristic data are shown in Table I.

EXAMPLE 7

The procedure of Example 4 is followed, but the so-called "original precipitated silica suspension" of Example 1 is diluted, by means of additional water, to 13 g of precipitated silica/l and 8.5 g of $Na_2SO_4$/l. On the other hand, the addition of 92.7 ml of water/min during the precipitation is dispensed with. The resulting precipitated silica content is 64 g/l. The characteristic data of the precipitated silica obtained are shown in Table I.

EXAMPLE 8

The procedure of Example 7 is followed except that the precipitation is carried out at 95° C. and also the precipitation time is reduced from 60 to 45 minutes. A precipitated silica content of 52 g/l results. The characteristic data of the precipitated silica obtained are shown in Table I.

EXAMPLE 9

First, an "original precipitated silica suspension" is prepared according to Example 1, this suspension having a precipitated silica content of 80 g/l, an $Na_2SO_4$ content of about 52 g/l and a pH of 8.5. However, in contrast to Example 1, the mixture is subjected to intensive shearing over the entire precipitation period of 90 minutes, by means of a circulating pump which recirculates the contents of the vessel several-fold. Further details of the apparatus used and of the shearing conditions are to be found in German Pat. No. 1,767,332, in particular in column 8, lines 31–68 thereof.

This subject matter is reproduced below:

EXAMPLE 1

To carry out the process, a precipitation apparatus is used, which is equipped with a dispersing device in addition to the known standard apparatus. The dispersing device is either built into the precipitation vessel or operates continuously via a closed-circuit line as a disperser and pump. The throughput capacity of the dispersing pump is adapted to the total precipitation volume of the attachment (about 100 liters). A dispersing device with a drive motor which delivered 3 kW at 8000 rpm was used. The pump power output of the machine, in terms of water, is 2000 kg/h. Hence, the throughput rate is 20 ($h^{-1}$).

The process is not practiced exclusively with this special machine, but can be carried out with any other disperser of similar construction, as well as with ultrasonic dispersers.

For the precipitation, 67.5 liters of hot water and 10.48 liters of soluble soda glass (density 1.17 $g/cm^3$ ratio $SiO_2:Na_2O = 3.30$) is heated, with stirring, to 82.5° C. Into this alkaline precipitation batch there are metered simultaneously, during the following 90 minutes, with stirring and dispersion, soluble soda glass (d=1.35 $g/cm^3$ ratio $SiO_2:Na_2O=3.30$) at 11 L/h and 55.5% $H_2SO_4$ (density: 1.45 $g/cm^3$) at 1.9 L/h. During this phase of the reaction, the contents of the vessel are pumped through the disperser 30 times. Thereafter, the silicic acid suspension is adjusted to a pH of 3.5 by the addition of 55.5% sulfuric acid (density: 1.45 $g/cm^3$); this is accomplished with an acid flow of 2.5 L/h for 35 minutes.

Dispersion is continued even during this phase of the reaction. Yield: 8 kg of silicic acid. Energy consumption: about 0.42 kW-h/kg $SiO_2$. Dispersion density 31.6 kW-h/$m^3$. The washed filter cake is dried at 110° to 120° C. and ground using a pinned-disk mill.

The silicic acid is in the form of a very finely dispersed white powder, which is characterized by the following values:

| | |
|---|---|
| loss of ignition (1000° C.) | 10.5% wt. % |
| $SO_4^{-2}$ content | 0.08 wt. % |
| pH (4% suspension) | 6.2 |
| bulk density | 78 g/L |
| DBP number (structure) | 2.84 mL/g | particle size distribution (Bahco analysis):
60.3 wt. % <2.1 microns
93.7 wt. % <3.4 microns
98.4 wt. % <6.9 microns
99.9 wt. % <24.9 microns.

The original precipitated silica suspension thus prepared is diluted with water to a precipitated silica content of 20 g/l and an $Na_2SO_4$ content of 13 g/l. 10.5 liters of this suspension serve as the original charge for the subsequent precipitation, which is carried out according to Example 3. The resulting precipitated silica content is 49 g/l. The characteristic data of the precipitated silica are shown in Table I. It emerges from the table that as a result of the shearing action the abrasiveness and tamped density of the precipitated silica are substantially increased compared to the corresponding values for a precipitated silica prepared using a non-sheared original precipitated silica suspension.

EXAMPLE 10

The procedure of Example 9 is followed, the sole difference being that the precipitation time is increased from 30 to 60 minutes. A precipitated silica content of 64 g/l results. Once again, a significant increase in abrasiveness (by 92%) and in tamped density (by 24%) is achieved.

EXAMPLE 11

This example is intended to illustrate the industrial production of the precipitated silica according to the invention:

First, an original precipitated silica suspension have a pH of 8.5, a precipitated silica content of about 85 g/l and an $Na_2SO_4$ content of about 55 g/l is prepared, using the recipe of Example 1, adjusted to the volume available, in a 70 $m^3$ wooden precipitation vessel equipped with a beam stirrer. 8 $m^3$ of this suspension are subsequently left in the wooden vessel and mixed with 26 $m^3$ of hot water to form an initial precipitation charge containing about 20 g of precipitated silica/l and about 13 g of $Na_2SO_4$/l, this charge being heated to 85° C. While keeping the temperature and the pH of 8.5 constant, 8.8 $m^3$ of sodium silicate solution (density: 1.353 g/ml, $SiO_2:Na_2O$ ratio=3.46), 0.90 $m^3$ of concentrated (96% strength) sulfuric acid and 19.0 $m^3$ of hot water are simultaneously metered into the initial precipitation charge, over a period of 45 minutes. After completion of precipitation, the suspension is brought to a pH of 3.5 within a few minutes, using concentrated (96% strength) sulfuric acid. The resulting precipitated silica content is about 64 g/l.

For further processing, the precipitated silica is isolated from the suspension by means of a filter press, washed, dried in a multi-daylight drier and milled in a pendulum roller mill. The characteristic data of the precipitated silica obtained are shown in Table I.

EXAMPLE 12

The apparatus employed corresponds to that of Example 11. First, an "original precipitated silica suspension" having a pH of 8.5, a precipitated silica content of about 85 g/l and an $Na_2SO_4$ content of about 55 g/l is prepared as described in Example 11.

10 $m^3$ of this suspension are subsequently left in the 70 $m^3$ wooden vessel and mixed with 27 $m^3$ of hot water to give an initial precipitation charge, containing about 23 g of precipitated silica/l and 15 g of $Na_2SO_4$/l, which is heated to 85° C. At this temperature, and while maintaining a pH of 8.5–9.0, 9.6 $m^3$ of sodium silicate solution (density: 1.353 g/ml; $SiO_2:Na_2O$ ratio=3.46), 0.94 $m^3$ of concentrated (96% strength) sulfuric acid and 20.0 $m^3$ of hot water are metered simultaneously, over 80 minutes, into the initial charge. After completion of precipitation, the suspension is brought to a pH of 3.5 with concentrated (96% strength) sulfuric acid. The precipitated silica content is 64 g/l.

For further processing, the precipitated silica is isolated from the suspension by means of a filter press, washed, dried in a multi-daylight drier and steam jet-milled in a Jet-O-mizer, type 0808. The milling throughput is 500 kg/h, under a milling pressure of 8.5 bar. The characteristic data of the precipitated silica obtained are shown in Table I.

EXAMPLE 13

The procedure of Example 11 is followed, the sole difference being that milling is effected differently, namely by means of a steam jet mill under the conditions stated in Example 12.

EXAMPLE 14

The procedure of Example 12 is followed, but the precipitation time is extended from 80 to 110 minutes. The dosed amounts of concentrated sulfuric acid, hot water and sodium silicate solution are adapted accordingly. The precipitated silica content, after completion of precipitation, is 64 g/l. The steam jet milling conditions were also modified, namely to a throughput of 630 kg/h and a milling pressure of 11 bar.

Table I described the physicochemical characteristics of the precipitated silicas prepared according to Examples 1 to 14. The data of Example 1 are those for a comparative example according to the prior art which results in the preparation of a precipitated silica having inadequate abrasiveness and a low tamped density.

The physicochemical data of the precipitated silicas obtained according to Examples 2 to 10 relate to the products from laboratory processes, while the data of Examples 11 to 14 are material data for precipitated silicas from production processes.

The specific BET surface area, tamped density and lightness value A are determined by DIN methods. As regards the Cu abrasion measurement and the determination of the ALPINE screen retainings of $>63\mu$, the methods are described below.

DETERMINATION OF THE CU ABRASION IN 10% STRENGTH GLYCEROL DISPERSION (a) Preparation of the glycerol dispersion 153 g of anhydrous glycerol (German Pharmacopeia 7; density=1.26) are weighed out into a 250 ml polyethylene beaker. 17 g of precipitated silica are carefully mixed into the glycerol by means of a spatula. The mixture is then homogenized by means of a paddle stirrer (diameter 5.2 cm) for 12 minutes at 1,500 rpm.

(b) Method of abrasion measurement

The abrasion is measured in the abrasion tester disclosed in the following publications:

(1) Pfrengle: Fette, Seifen, Anstrichmittel, 63 (5) (1961), pages 445 to 451 "Abrasion und Reinigungskraft von Putzkörpern in Zahnpasten" ("Abrasion and Cleansing Power of Polishing Agents in Toothpastes")

(2) A. RENG and F. DANY, Parfümerie und Kosmetik 59 (2) (1978), pages 37 to 45; "Anwendungstechnische Prüfung von Zahnpasten" ("Performance Testing of Toothpastes").

For this purpose, the 6 troughs of the test apparatus were each covered with 20 ml of the homogeneous dispersion. The abrasion produced by six plane-ground nylon brushes on six plane-ground Cu sheets (electrolytic copper) in five hours as a result of 50,000 reciprocating strokes is determined by differential weighing. In calculating the abrasiveness, the means of the values obtained are taken. The abrasion (abrasiveness) is quoted in mg of Cu.

DETERMINATION OF THE SCREEN RETAININGS, USING THE ALPINE AIR JET SCREEN

To determine the screen retainings, the precipitated silica is screened through a $500\mu$ screen in order to do away with any deaeration nodes which may be present. 10 g of the screened material are then placed on a particular air jet screen and are screened under 200 mm water-column suction. Precipitated silica particles which settle on the acrylic cover of the screening apparatus are removed by repeatedly tapping the knob of the screen cover. Screening has ended when the retainings stay constant, this being generally discernible from their free-flowing appearance. To make sure, screening is then continued for a further minute. In general, the screening process requires five minutes. In the case of materials composed of particles of $<500\mu$, the sample is not screened beforehand but instead is placed directly on the air-jet screen. If any agglomerates should form, the screening process is briefly interrupted and the agglomerates are destroyed by light pressure with a brush. After screening, the screen retainings are carefully tapped off the air-jet screen and reweighed.

Calculation: The screen retainings are recorded as a percentage, stating the mesh width of the screen.

Apparatus: Alpine air-jet screen, laboratory type S 200 air jet screen, with DIN 4,188 screen fabric.

Test of rheological activity of abrasive silica in a 30% strength dispersion in a 1:1 glycerol/water mixture; Brookfield RTV Sp5

| 1. Test mixes | 60 g of silica |
| --- | --- |
| | 70 g of anhydrous glycerol, German Pharmacopeia 7, density 1.26 ml/g |
| | 70 g of distilled water |
| | 200 g of a 30% strength dispersion of silica |

2. Method

The abrasive silica is stirred manually into the glycerol/water mixture in a 400 ml beaker (squat form), stirring being effected with a glass rod for 1 minute. The mixture is left to stand for 24 hours and the viscosity is then measured.

3. Measurement

The viscosity measurement is carried out in the same beaker, using the Brookfield RVT viscometer, with spindle 5 at various rates of revolution per minute.

4. Calculation

Scale reading×factor=viscosity in mPa.s.

The above identified German applications and patents, especially DAS 1,467,019 and PS 1,767,332 are relied on and incorporated herein by reference.

Following the table is a reproduction of a certified English language translation of the DE-AS 1467019. The figure referred to therein is the figure which appears in DE-AS 1467019.

TABLE I

| Physiochemical characteristic | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Physiochemical characteristic data of the precipitated silicas prepared according to Examples 1 to 14 ||||||||||||||
| BET surface area, DIN 66,131, m²/g | 186 | 73 | 78 | 41 | 24 | 40 | 58 | 40 | 48 | 18 | 103 | 70 | 101 | 51 |
| Tamped density, DIN 53,194, g/l | 80 | 98 | 172 | 244 | 345 | 218 | 111 | 210 | 520 | 645 | 270 | 138 | 110 | 156 |
| ALPINE screen retainings > 63μ, % by weight | 1.2 | 0.3 | <0.1 | 0.1 | <0.1 | <0.1 | 0.2 | <0.1 | <0.1 | <0.1 | 1.4 | <0.1 | <0.1 | <0.1 |
| Cu abrasion in 10% strength glycerol dispersion, mg | <1 | 11 | 7 | 23 | 27 | 19 | 16 | 18 | 13 | 25 | 14 | 12 | 8 | 17 |
| Lightness value A DIN 55,912, % | 96.3 | 96.0 | 95.8 | 91.0 | 87.8 | 92.7 | 94.7 | 93.5 | 93.2 | 89.6 | 94.4 | 95.7 | 96.8 | 94.6 |

The invention relates to a process for synthesis of finely divided silica by reaction of alkali metal silicate solutions with an acid solution while preventing gel formation, the alkali metal silicate and acid solutions being added simultaneously into a deposited aqueous alkali metal silicate solution, after which the resulting silica is separated from the adhering solution, washed, dried and ground.

For the production of finely divided silica, there have been published a number of processes in which a mineral acid is added to a deposited alkali metal silicate solution in the presence of neutral salts of strong acids and strong bases such as, for example, sodium chloride or sodium sulfate. The procedure followed in this case is, for example, that specified minimum salt concentrations are maintained in the deposited solution and the precipitation initial salt concentration to the final salt concentration is between 1:1.5 and 1:5.0. According to another procedure, there is used as the deposited solution a solution of inert electrolytes, into which the two reaction components are introduced simultaneously but at different places. In this case, the electrolyte quantities at the start of precipitation and during precipitation are to amount respectively to at least 1% and at least 5% of the total reaction mixture. If the precipitation process is conducted such that the water added with the reagents causes no concentration change in relation to the additional electrolytes in the reaction mixture, the reaction solution after separation of the formed silica can be reused for new charges in a continuous process.

It is also already known that silica filler materials with specified, adjustable specific particle surface areas can be synthesized by controlling the rate of addition of the acid in specified manner as a function of temperature, alkali metal silicate solution and electrolyte concentration of the starting solution and conducting the precipitation up to a pH of approximately 5. In this case, the reaction temperature can be as high as 90° C. For stabilization of such silica products, a heat treatment at temperatures of 120° to 140° C. or a further acid treatment in the presence of added aluminum sulfate has been performed. The acid post-treatment can be further continued until the content of $Na_2O$ in the silica has been lowered to below 1%.

Another known process for synthesis of a silica gel built up from growth nuclei is conducted by heating a stagnant silica sol to approximately 60° C. to obtain nuclei of high molecular weight silica hydrate and the mixing this solution of nuclei with the aqueous suspension of a silica solution, precipitated at a pH of 8 to 10.7 from an alkali metal silicate solution by means of mineral acids.

Many of these processes, especially the last-named, are cumbersome and offer no unconditional guarantee of homogeneous precipitation of the filler particles in terms of the size and condition of the surface. Moreover, the described continuous mode of operation cannot always be employed with satisfactory results, because the continuous reprecipitation of the electrolyte-containing filtrate, which contains entrained particles which have already been precipitated, causes premature digestion of the fresh precipitate and thereby unfavorably influences the texture of the precipitated particles.

The object of the invention was to provide a process for synthesis of finely divided silica by reaction of alkali metal silicate solutions with an acid solution while preventing gel formation, the alkali metal silicate solution and the acid solution being injected simultaneously into a deposited aqueous alkali metal silicate solution, after which the resulting silica is separated from the adhering solution and washed, dried and ground, and a sufficiently stable, digestion-insensitive, extremely finely divided and highly active silica is obtained in simple manner in a single precipitation process.

The characterizing feature of the invention is to be seen in the fact that, for precipitation of the silica in a deposited alkali metal silicate solution with a concentration of approximately 5 to 25 g, preferably 5 to 10 g of $SiO_2$ per liter of solution, the acid solution and the alkali metal silicate solution are injected with specified solution concentrations and specified feed rates and with maintenance of a precipitation temperature of between 80° and 90° C. in the reaction medium such that, for a period of at least 30% of the total precipitation time, the viscosity of the reaction medium is kept uniformly low and the pH is maintained between 10 and 12, and addition of the reagents is terminated only when the viscosity has passed through a maximum and decreased to a value of less than 100% higher than the starting viscosity.

The general variation with time of the viscosity in the reaction medium during precipitation is shown schematically in the figure.

In the figure, the viscosity is plotted against the time. The shape of the curve shows that the viscosity practically does not change from the start of addition of alkali metal silicate and acid, i.e. beginning with time zero (point A) up to the 33rd minute of the precipitation process (point B). Thereafter, there begins a steep rise, which leads to a maximum at approximately 11.5 scale divisions (point C). The viscosity remains in this maximum range for only a short period, which in fact is approximately 10 minutes, while the silica precipitates.

From point D on, i.e., approximately 50 to 60 minutes after the start of addition, the viscosity decreases rapidly at first and then more slowly starting from 60 to 65 minutes after the start of addition, and in the 96th minute reaches a value of 3.8 scale divisions, which therefore is less than 100% higher than the starting viscosity.

At point E, the addition of the reaction solutions is terminated. The time of 39 minutes corresponding to the section A-B amounts to 44.4% of the total precipitation time, which lasts for 96 minutes.

In the work of Iler, "Colloid Chemistry of Silica and Silicates", 1955, general statements are indeed made regarding the parameters by which the precipitation of silica from water glass solution can be influenced, but it is not obvious from this treatise that the higher viscosity, known in itself, of the reaction liquid before the start of silica precipitation exerts a decisive influence on the physical condition of the precipitated product. A certain influence by the viscosity is indeed made possible according to the teaching of German Patent 867,543, wherein dilute acid is introduced with vigorous stirring into a deposited alkali metal silicate solution; however, the procedure is difficult and is conducted only while maintaining different feed rates, as the practical example shows. Accordingly, the precipitation process is effected in three times periods, referred to as precipitation periods, in each case with different rate of feed of acid. Thus, in addition to the precipitation conditions already indicated in general in Iler's treatise, there occurs yet another parameter which influences the fate of the precipitated products; namely, the feed rate, which, however, according to the teaching of German Patent 867,543, is varied and not, as in the present process, uniform.

According to the procedure of the invention, it is possible from the start of precipitation to keep the viscosity variation under control and to regulate it by, so to speak, infinite dilution.

The technical rule regarding the manner in which the viscosity can be kept low consists in the present invention in the simultaneous addition of the reaction components to an original volume of water which has been made alkaline to a specified pH (10 to 12), in specified solution concentrations, in specified feed rate and in maintenance of a precipitation temperature between 80° and 90° C., as follows from the cited example.

Only be noting the viscosity variation in the sense of the process according to the invention is it possible in a continuous operation to achieve large-scale production of an active silica which always has homogeneous particle-scale distribution and identical specific surface, i.e. which therefore always has uniform activity. Precipitation processes in which one of the two reagents is used as deposited solution, e.g., according to French Patent 1,064,230, in which the alkali metal silicate solution is used as the original solution, or according to the process of German Patent 946,433, in which the precipitation of the silica is effected from alkali silicate solution at a pH of 6 to 8, produce different conditions and thus are different in principle from the process according to the invention.

In general, the concentrations of the dilute alkali metal silicate solution as the original solution in the reaction vessel are not supposed to exceed approximately 25 g of $SiO_2$ per liter of solution. It is appropriate to maintain concentrations between 5 and 10 g of $SiO_2$ per liter. On the other hand, the alkali metal silicate solution which is added to the dilute deposited solution is supposed to contain a concentration of more than 50 g per liter, preferably 60 to 250 g of $SiO_2$ per liter. Furthermore, the addition of this silicate solution to the original solution is continued until the precipitation solution contains approximately at least 50 g of $SiO_2$ per liter. However, concentrations of more than 150 g of $SiO_2$ in the precipitation solution are in general not exceeded.

To achieve the best results, care is to be taken that the starting solution of alkali metal silicate is practically free of growth nuclei. This means that the reaction vessel is to be kept correspondingly clean.

In order to improve the stability of the product, it is permissible after the precipitation process to adjust the pH to approximately 7 by further acid addition. By further addition of concentrated acid, a pH of below 5, e.g., of approximately 2.5, can be adjusted. Thereafter, the silica is separated from the liquid.

According to the process of the invention, a pure silica is obtained with a particle size between 0.01 and 0.03 micron and a specific surface greater than 200 $m^2/g$, especially between 240 and 260 $m^2/g$, measured by the BET method. By means of a temperature treatment, the specific surface can be decreased to, for example, 100 to 150 $m^2/g$. The products after drying and grinding can be dispersed easily and in good distribution in elastomers. Vulcanized products consisting of natural or synthetic rubber and reinforced with the fillers obtained according to the invention, because of the ultrafine dispersion of the filler particles, have high transparency and are characterized by their good mechanical properties.

EXAMPLE

To conduct the process according to the invention, 11.5 liters of water at 80° C. is placed as deposited solution in a vessel of 80 liters capacity and mixed up to a pH of 11 with a dilute water glass solution. Thereafter, a sodium silicate solution (mole ratio of $Na_2O:SiO_2=1:3.35$) with a specific gravity of 1.088 and a sulfuric acid solution containing 90 g of $H_2SO_4$ per liter are injected simultaneously into the original solution at 86° C. within 100 minutes. Meanwhile, the viscosity rises from 2.2 units to 11.5 units. After reaching the point G, it decreases to 3.8 units. The addition of acid and water glass is continued for a period of approximately 100 minutes while the said pH range is maintained. The precipitation solution contains approximately 50 g of $SiO_2$ per liter. It is then acidified to a pH of 7 and subsequently to a pH of 2.5. The silica obtained after separation of the water and drying is extremely finely divided and has a specific particle surface of approximately 250 $m^2/g$, the particle size being in the range between 0.01 and 0.03 micron.

Instead of sulfuric acid, the precipitation process can also be effected using other substances which react as acids. Examples for this purpose are carbon dioxide, hydrochloric acid and ammonium chloride.

We claim:

1. A process for the preparation of a precipitated silica having the following physical-chemical characteristics:

| | | |
|---|---|---|
| BET surface area determined according to DIN 66,131 | $m^2/g$ | 15–110 |
| Tamped density determined according to DIN 53,194 | g/l | 150–750 |
| Cu abrasion in 10% strength glycerol dispersion | mg | 5–30 |
| Lightness value A according to DIN 55,921 | % | 86–96 |
| Particle size distribution curve of the secondary particles according to FIG. 1, using the | | |

| | | |
|---|---|---|
| Coulter Counter "ALPINE screen retainings" >63 μm | % by weight | <1.5 |
| Viscosiy of a 30% strength dispersion in a L;L glycerol/ water mixture (Brookfield RTV, Sp5) mPa.s | | 30,000–60,000 | comprising:
preparing a precipitated silica suspension by precipitating silica from an initial charge of sodium silicate solution having a concentration of about 5–25 g of $SiO_2$ per liter of solution by the simultaneous addition to said silicate solution of sulfuric acid and sodium silicate of particular concentration at particular feed rate defining precipitation conditions to thereby form a reaction medium suspension while maintaining a precipitation temperature in the reaction medium between 80° and 90° C.,
maintaining the pH of the reaction medium between 10 and 12 during the precipitation by said simultaneous addition,
said precipitation conditions being such that the viscosity of the reaction medium is kept for at least 30% of the total precipitation time uniformly low and the pH is maintained between 10 and 12 and during said simultaneous addition the viscosity of the reaction medium changing by rapidly rising to a higher viscosity than the viscosity value before said simultaneous addition and passing through a maximum viscosity value and then rapidly decreasing to a lower viscosity value,
thereafter terminating the simultaneous addition of said acid and silicate solution, said terminating occurring only when the viscosity has passed through a maximum and decreased to a value less than 100% higher than the viscosity of the reaction medium prior to said simultaneous addition,
diluting the precipitated silica suspension obtained thereby with hot water to obtain a precipitated silica content of 10–30 g/l and a sodium sulfate content of 6–20 g/l of $Na_2SO_4$, in said suspension,
heating said suspension to 85°–95° C., the pH of said suspension being brought to 7–9 by addition of sulfuric acid
and, while keeping this pH value of 7–9 constant, adding simultaneously sodium silicate solution, sulfuric acid and, if necessary, hot water over a precipitation period of 15 to 180 minutes so as to give a final concentration of precipitated silica of 40 to 80 g/l,
acidifying the suspension with concentrated sulfuric acid to a pH below 7,
and separating the precipitated silica from the suspension and subsequently milling the silica by a pendulum roller mill.

2. The process of claim 1, wherein the separation of the precipitated silica from the suspension is by means of a filter press.

3. The process of claim 1, further comprising subjecting the precipitated silica, after separation from the suspension to washing and drying.

4. A process according to claim 1, wherein prior to diluting the precipitated silica suspension with hot water, the reaction medium suspension is subjected to intensive shearing over the entire stage of its preparation up to the time that it is diluted with hot water.

5. A process for the preparation of a precipitated silica having the following physical-chemical characteristics:

| | | |
|---|---|---|
| BET surface area determined according to DIN 66,131 | $m^2/g$ | 15–110 |
| Tamped density determined according to DIN 53,194 | g/l | 90–650 |
| Cu abrasion in 10% strength glycerol dispersion | mg | 5–30 |
| Lightness value A according to DIN 55,921 | % | 90–96 |
| Particle size distribution curve of the secondary particles according to FIG. 2, using the Coulter Counter | | |
| "ALPINE screen retainings" >63 μm | % by weight | <0.1 |
| Viscosiy of a 30% strength dispersion in a 1:1 glycerol/ water mixture (Brookfield RTV, Sp5) mPa.s | | 30,000–60,000 | comprising:
preparing a precipitated silica suspension by precipitating silica from an initial charge of sodium silicate solution having a concentration of about 5–25 g of $SiO_2$ per liter of solution by the simultaneous addition to said silicate solution of sulfuric acid and sodium silicate of particular concentration at particular feed rate defining precipitation conditions to thereby form a reaction medium suspension while maintaining a precipitation temperature in the reaction medium between 80° and 90° C.,
maintaining the pH of the reaction medium between 10 and 12 during the precipitation by said simultaneous addition,
said precipitation conditions being such that the viscosity of the reaction medium is kept for at least 30% of the total precipitation time uniformly low and the pH is maintained between 10 and 12 and during said simultaneous addition the viscosity of the reaction medium changing by rapidly rising to a higher viscosity than the viscosity value before said simultaneous addition and passing through a maximum viscosity value and then rapidly decreasing to a lower viscosity value,
thereafter terminating the simultaneous addition of said acid and silicate solution, said terminating occurring only when the viscosity has passed through a maximum and decreased to a value less than 100% higher than the viscosity of the reaction medium prior to said simultaneous addition,
diluting the precipitated silica suspension obtained thereby with hot water to obtain a precipitated silica content of 10–30 g/l and a sodium sulfate content of 6–20 g/l of $Na_2SO_4$, in said suspension,
heating said suspension to 85°–95° C., the pH of said suspension being brought to 7–9 by addition of sulfuric acid
and, while keeping this pH value of 7–9 constant, adding simultaneously sodium silicate solution, sulfuric acid, and if necessary, hot water over a precipitation period of 15 to 180 minutes so as to give a final concentration of precipitated silica of 40 to 80 g/l,
acidifying the suspension with concentrated sulfuric acid to a pH below 7, and separating the precipitated silica from the suspension and subsequently milling the silica by a jet mill.

6. The process of claim 5, wherein the separating of the precipitated silica from the suspension is by means of a filter press.

7. The process of claim 5, further comprising subjecting the precipitated silica, after separation from the suspension to washing and drying.

8. A process according to claim 5, wherein prior to diluting the precipitated silica suspension with hot water, the reaction medium suspension is subjected to intensive shearing over the entire stage of its preparation up to the time that it is diluted with hot water.

* * * * *